US00PP14771P3

(12) United States Plant Patent
Amorao et al.

(10) Patent No.: US PP14,771 P3
(45) Date of Patent: May 11, 2004

(54) STRAWBERRY PLANT NAMED 'DRISCOLL CAMARILLO'

(50) Latin Name: *Fragaria×ananassa*
Varietal Denomination: Driscoll Camarillo

(75) Inventors: Amado Q. Amorao, Camarillo, CA (US); Arnoldo Solis, Jr., Oxnard, CA (US); Michael Ferguson, Chatsworth, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 8 days.

(21) Appl. No.: 10/077,153

(22) Filed: Feb. 15, 2002

(65) Prior Publication Data

US 2003/0159190 P1 Aug. 21, 2003

(51) Int. Cl.[7] ..... A01H 5/00

(52) U.S. Cl. ..... Plt./209

(58) Field of Search ..... Plt./208, 209

*Primary Examiner*—Bruce R. Campell
*Assistant Examiner*—Susan B. McCormick
(74) *Attorney, Agent, or Firm*—Pennie & Edmonds LLP

(57) ABSTRACT

This invention relates to a new and distinct variety of strawberry named 'Driscoll Camarillo'. The variety is similar to the varieties 'Baeza' and 'Ventura'. The variety is distinguished from 'Baeza' and 'Ventura' in that 'Driscoll Camarillo' has a longer fruiting truss, a dark green coloration of the upper side of the leaf, a globosely plant habit, even fruit coloration, and absent to small hollow center size.

5 Drawing Sheets

Latin name of the genus and species of the plant claimed: *The variety is botanically identified as Fragaria×ananassa.*

BACKGROUND OF THE INVENTION

The new variety originated as a result of a controlled cross between the strawberry plants 'Baeza' (U.S. Plant Pat. No. 11,548) and '33×257' (unpatented variety of Driscoll Strawberry Associates, Inc.) in an ongoing breeding program, and was discovered in Ventura County, Calif. in October, 1997. The original seedling of the new cultivar was asexually propagated by solons in a nursery in Shasta County, Calif. Propagates were transplanted to a controlled breeding plot in Ventura County, Calif., where the variety was identified and selected for further evaluation. 'Driscoll Camarillo' was subsequently asexually propagated and underwent further testing Ventura County, California for five years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Camarillo'. The variety is botanically identified as *Fragaria×ananassa*. The new variety is distinguished from other varieties by a number of characteristics as set forth in Tables 1–4.

COMPARISON TO SIMILAR VARIETIES

The varieties which we believe to be similar to 'Driscoll Camarillo' from those known to us are 'Baeza' (U.S. Plant Pat. No. 11,548) and 'Ventura'. There are several characteristics of the new variety that are different from, or not possessed by 'Baeza' and 'Ventura'. The new variety has a longer fruiting truss, a dark green coloration of the upper side of the leaf, a globosely plant habit, even fruit coloration, and an absent to small hollow center size.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
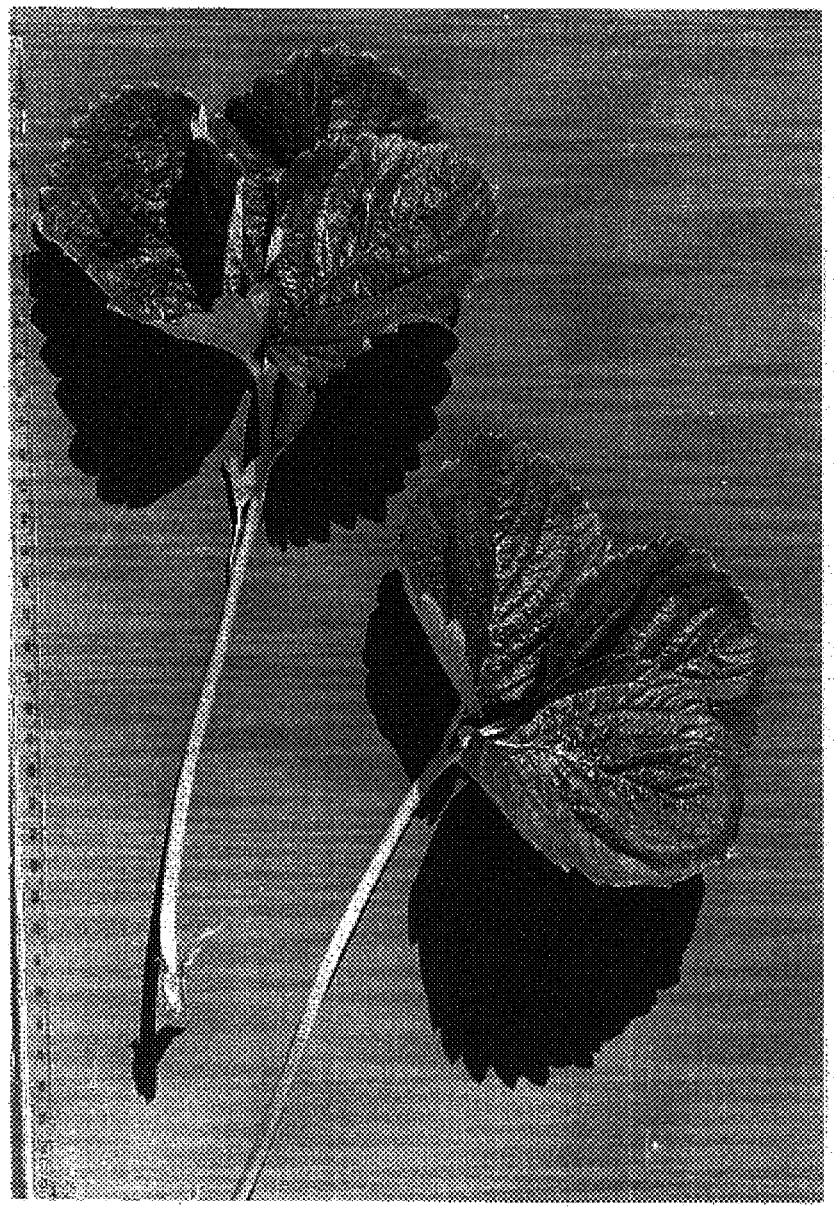
FIG. 1 shows the leaves of the plant.
Figure 2:
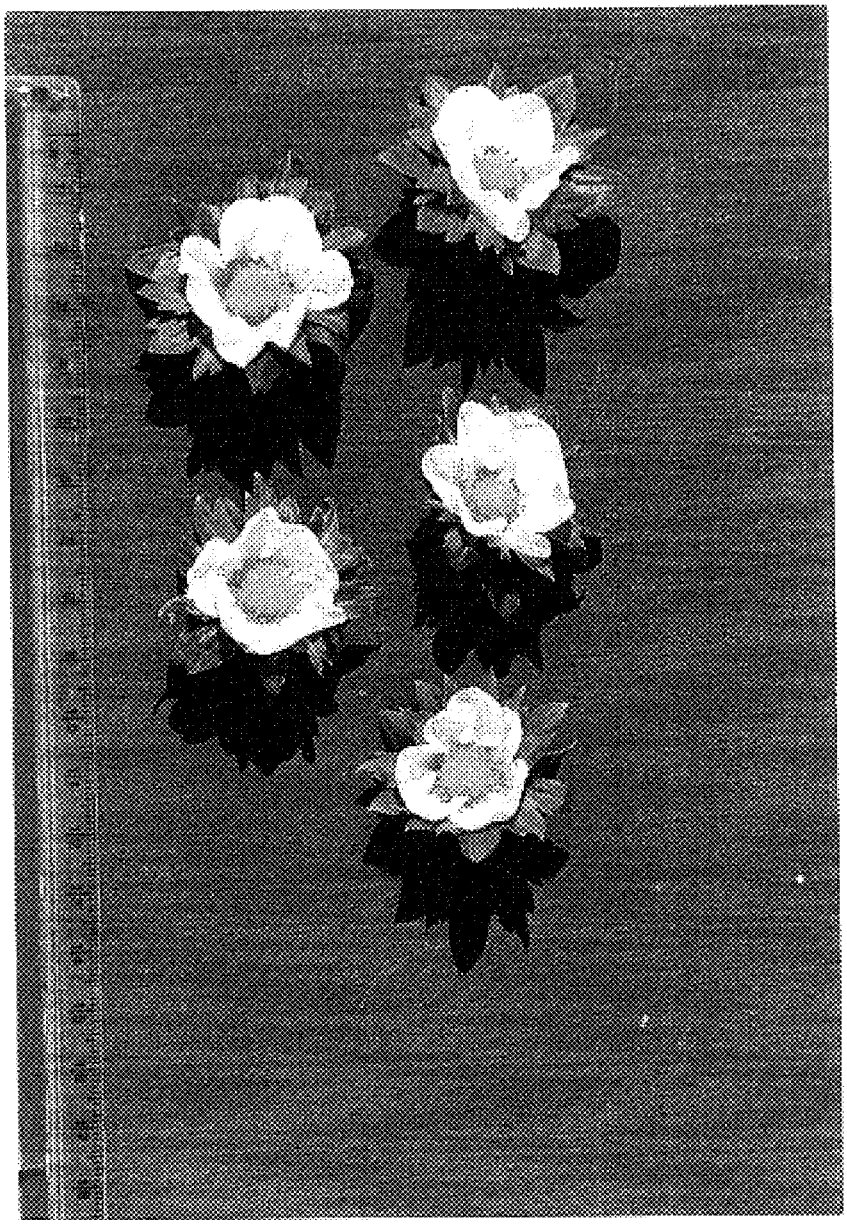
FIG. 2 shows the upper side.
Figure 3:
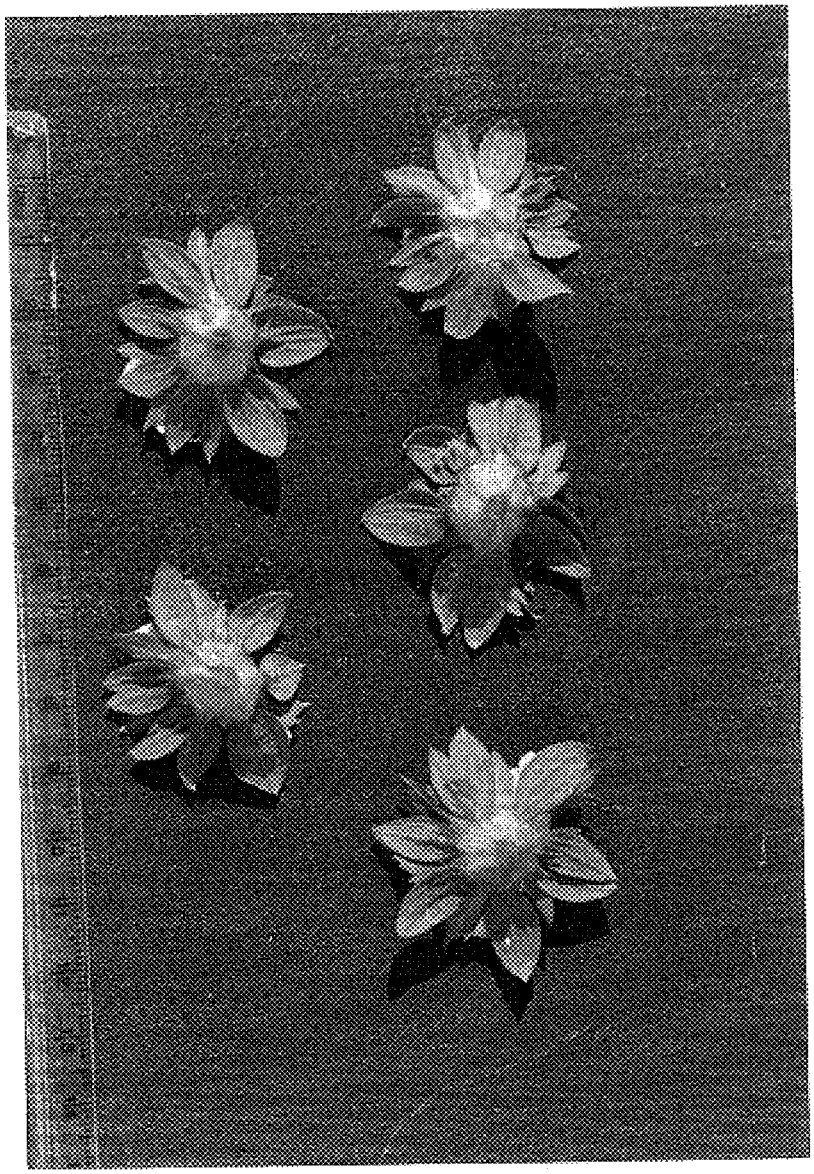
FIG. 3 shows the under side of the flowers.
Figure 4:
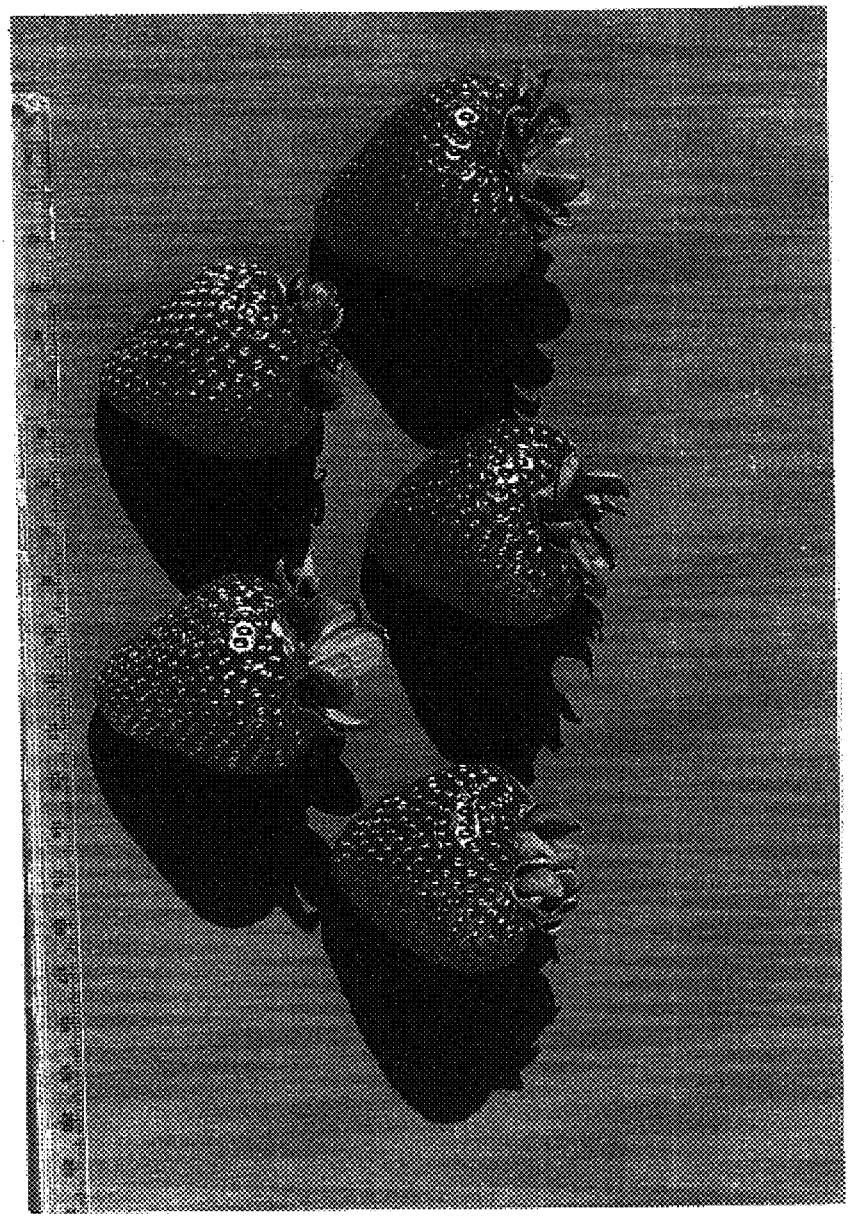
FIG. 4 shows a close-up of the fruit.
Figure 5:
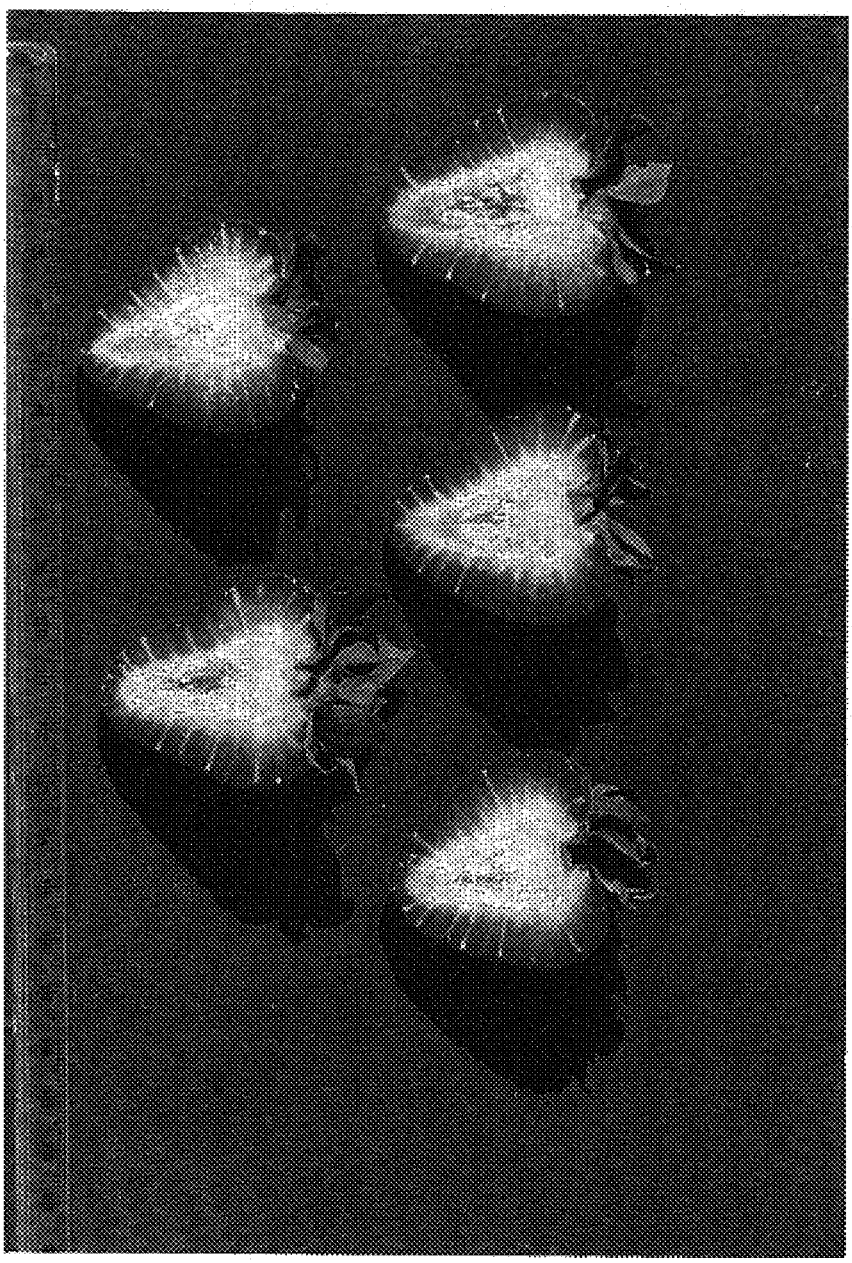
FIG. 5 shows the fruit in longitudinal cross-section.

The following detailed description of the new variety is based upon observations taken of plants and fruit grown in Ventura County, Calif., U.S.A. Observations of 'Driscoll Camarillo', 'Baeza' and 'Ventura' were taken in side by side comparison in 2001. This description is in accordance with UPOV terminology. Color designations, color descriptions, and other phonotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of solons. Although propagation by solons is presently preferred, other known methods of propagating strawberry plants may be employed.

CHARACTERISTICS OF THE NEW VARIETY

Information on the new variety is presented in Tables 1, 2 and 3. In the tables, the flowers described are secondary flowers except where indicated. The fruit described is the secondary fruit on one year old plants. Fruit and flower measurements are an average of both primary and secondary fruit and flowers. The leaf width is 14.78 cm and the leaf length is 9.98 cm. The leaf margin is crenate, and the leaf texture is very strongly blistered. The petiolule length is 16.22 mm, the petiolule diameter is 2.22 mm, and the petiolule color is 149A (in The R.H.S. Colour Chart). The anthocyanin color on stolons is 60C (in R.H.S. Colour Chart). The stolon thickness is 3.875 mm. The sepal length is 9.18 mm, sepal diameter is 5.4 mm, and sepal color is 146B (in R.H.S. Colour Chart). The reproductive organs are typical for the species. The color of the anthers is Yellow 13A (in R.H.S. Colour Chart), and the color of the pistils and receptacle are Yellow 7A (in R.H.S. Colour Chart). The average achene weight is 0.0054 g, and there are an average number of 224 achenes per berry.

Table 1 provides a quantitative comparison of the plant and fruit characteristics of the new variety 'Driscoll Camarillo' compared with characteristics of 'Baeza' and 'Ventura'. Table 2 provides additional information of the plant and fruit characteristics of the new variety 'Driscoll Camarillo' compared with characteristics of the varieties 'Baeza' and 'Ventura'. Table 3 provides reactions of the new variety to stresses, pests and disease as compared to the varieties 'Baeza' and 'Ventura'. Table 4 provides isozyme characteristics of the new variety as compared to the varieties 'Baeza' and 'Ventura'.

TABLE 1

DETAILED COMPARISON OF CAMARILLO, BAEZA AND VENTURA

| | CAMARILLO | BAEZA | VENTURA |
|---|---|---|---|
| Plant Characteristics | | | |
| Height of Plant (cm) | 23.3 | 20.8 | 21.0 |
| Spread of Plant (cm) | 42.7 | 38.2 | 38.7 |
| Number of Crowns | 4.8 | 3.0 | 3.3 |
| Leaf Characteristics | | | |
| Terminal Leaflet Length (cm) | 8.2 | 8.5 | 7.5 |
| Terminal Leaflet Width (cm) | 8.2 | 8.7 | 7.5 |
| Terminal Leaflet Length/Width | 1.0 | 0.98 | .99 |
| # Teeth/Terminal Leaflet | 24.8 | 25.4 | 22.4 |
| Color of upper side | dark green 147A | light to medium green 147A | medium green 137A |
| Color of under side | light green 138B | light green 138B | light green 138B |
| Petiole Length (cm) | 15.9 | 14.5 | 14.2 |
| Petiole Color | 149A yellow green | 144A yellow green | 145A yellow green |
| Bract Frequency | 42% mostly double | 67% mostly double | 50% mostly double |
| Stipule Length (cm) | 3.5 | 3.5 | 2.8 |
| Stipule Width (cm) | 1.2 | 1.1 | 1.1 |
| Stolon | | | |
| Diameter at base of last daughter | 4.09 | 4.12 | 4.05 |
| Flower Characteristics | | | |
| Petal Length (cm) | 1.22 | 1.10 | 1.19 |
| Petal Width (cm) | 1.39 | 1.22 | 1.09 |
| Petal Length/Width Ratio | 0.88 | 0.90 | 1.09 |

TABLE 1-continued

DETAILED COMPARISON OF CAMARILLO, BAEZA AND VENTURA

| | CAMARILLO | BAEZA | VENTURA |
|---|---|---|---|
| Petal color | 155B | | |
| Flower Diameter (cm) | 2.61 | 2.50 | 2.40 |
| Calyx Diameter (cm) | 2.98 | 2.55 | 2.57 |
| Fruiting Truss | | | |
| Length (cm) | 32.0 | 28.5 | 24.8 |
| Fruit Characteristics | | | |
| Fruit Length (cm) | 4.1 | 4.2 | 4.5 |
| Fruit Width (cm) | 4.0 | 3.8 | 4.0 |
| Fruit Length/Width Ratio | 1.03 | 1.11 | 1.11 |
| Average Berry Weight (g) | 21.1 | 21.5 | 24.3 |
| External Color | 46A red | 46A red | 46A red |
| Internal Color | 34B & 155A orange red & white | 42B & 155D white & orange red | 44A orange red |
| Average % brix | 9.26 | 10.38 | 9.27 |
| Brix/Acid Ratio | 12.62 | 12.87 | 12.95 |
| Achene Coloration | 184B and 13B | 13A and 46A | 13B and 45B |
| Marketable Yield in 2001 (g/plant) | 410 | 293 | 118 |

TABLE 2

CHARACTERISTICS OF CAMARILLO, BAEZA AND VENTURA

| | CAMARILLO | BAEZA | VENTURA |
|---|---|---|---|
| Plant | | | |
| Habit | globose | flat globose | globose to flat globose |
| Density | open | open | medium |
| Vigor | medium | medium | weak to medium |
| Leaf | | | |
| Shape in cross section | concave | concave | slightly concave |
| Interveinal blistering | very strong | strong to very strong | strong |
| Glossiness | medium to strong | weak | medium |
| Number of leaflets | three only | three only | three only |
| Terminal leaflet margin profile | revolute to flat | revolute to flat | revolute to flat |
| Terminal leaflet shape of base | rounded | obtuse to rounded | rounded |
| Terminal leaflet shape of teeth | rounded | acute to obtuse | obtuse |
| Stipule pubescence | sparse | sparse | sparse |
| Petiole pubescence | sparse | very sparse to sparse | sparse |
| Petiole pose of hairs | outwards | outwards | outwards |
| Stolon | | | |
| Amount | few to medium | few to medium | few to medium |
| Anthocyanin coloration | weak to medium | weak to medium | medium |
| Thickness | thick | thick to very thick | medium to thick |
| Pubescence | sparse | medium to dense | dense |
| Inflorescence | | | |
| Position relative to foliage | above | level to above | level to above |

TABLE 2-continued

CHARACTERISTICS OF CAMARILLO, BAEZA AND VENTURA

| | CAMARILLO | BAEZA | VENTURA |
|---|---|---|---|
| Diameter of calyx relative to corolla on secondary flowers | smaller to same size | same size to larger | smaller |
| Diameter of inner calyx relative to outer on secondary flowers | same size | same size | same size |
| Spacing of petals | overlapping | overlapping | touching to overlapping |
| Fruiting Truss | | | |
| Attitude at first picking | prostrate | prostrate | semi-erect |
| Fruit | | | |
| Predominant shape | cordate | conical | conical to cordate |
| Difference in shapes between primary and secondary fruits | slight | very slight to slight | slight |
| Band without achenes | absent or very narrow | very narrow to narrow | narrow |
| Unevenness of surface | weak | weak to medium | weak to medium |
| Evenness of color uneven | even | slightly uneven to even | slightly even |
| Glossiness | strong | strong | strong |
| Insertion of achenes | below surface | level to below surface | below surface |
| Insertion of calyx | in a basin | level | in a basin to level |
| Pose of the calyx segments | spreading | spreading to reflexed | reflexed |
| Size of calyx in relation to fruit on secondary fruit | smaller | same size to larger | smaller |
| Adherence of calyx | strong | strong | weak to medium |
| Firmness of flesh | firm | medium to firm | firm |
| Evenness of flesh color | slightly uneven | uneven | slightly uneven |
| Distribution of flesh color | marginal and central | marginal to central | marginal to central |
| Hollow center size | absent to small | large | small |
| Sweetness | medium | medium | medium to strong |
| Texture when tasted | medium | medium | fine |
| Acidity | medium | medium | weak to medium |
| Time of Flowering | mid to late August | mid to late August | mid to late August |
| Harvest Interval in 2001 (Week Ending) | 9/29–12/22 | 9/29–12/22 | 10/6–12/22 |
| Type of Bearing | fully everbearing | fully everbearing | fully everbearing |

REACTION TO STRESS, PESTS, AND DISEASE

TABLE 3

5.3 REACTION TO STRESS, PESTS, AND DISEASE

| | CAMARILLO | BAEZA | VENTURA |
|---|---|---|---|
| Reaction to Stress | | | |
| high pH | moderately resistant | moderately resistant | moderately resistant |
| high soil salt levels | moderately resistant | susceptible | moderately resistant |

TABLE 3-continued 5.3 REACTION TO STRESS, PESTS, AND DISEASE

| | CAMARILLO | BAEZA | VENTURA |
|---|---|---|---|
| Reaction to Pests | | | |
| *Tetranychus urticae* | moderately susceptible | moderately susceptible | moderately susceptible |
| *Lygus hesperus* | susceptible | susceptible | susceptible |
| Reaction To Diseases | | | |
| Botrytis fruit rot | susceptible | susceptible | moderately susceptible |
| Powdery mildew | susceptible | highly susceptible | highly susceptible |
| Verticillium wilt | susceptible | susceptible | susceptible |
| Strawberry Mottle Virus | moderately resistant | moderately resistant | moderately resistant |
| *Xanthomonas fragariae* | moderately resistant | moderately resistant | moderately resistant |

ISOZYME ANALYSIS

In addition to the morphological description above, the new cultivar 'Driscoll Camarillo' has been analyzed to obtain an indication of its genetic makeup to provide further means for identifying the new variety and distinguishing it from some other somewhat similar and/or related strawberry varieties. Specifically, leaf samples of 'Driscoll Camarillo', 'Baeza', and 'Ventura' were analyzed by electrophoresis for isozyme patterns of the enzymes phosphoglucoisomerase ("PGI"), leucine aminopeptidase ("LAP") and phosphoglucomutase ("PGM"). See *J. Amer. Soc. Hort. Sci.* 106:684–687. Isozyme characterization of the three varieties is presented in Table 4, with the letters representing the banding patterns for each enzyme as designated in the above-identified article.

TABLE 4

ISOZYME ANALYSIS FOR CAMARILLO, BAEZA AND VENTURA

| Locus | CAMARILLO | BAEZA | VENTURA |
|---|---|---|---|
| PGI | A2 | A1 | A2 |
| LAP | B3 | B3 | B3 |
| PGM | C4 | C3 | C4 |

What is claimed is:

1. A new and distinct variety of strawberry plant, substantially as shown and described.

* * * * *